United States Patent
Jankowski et al.

(10) Patent No.: US 8,142,465 B2
(45) Date of Patent: Mar. 27, 2012

(54) PATIENT'S SKIN PUNCTURING DEVICE

(75) Inventors: Andrzej Jankowski, Warsaw (PL); Adam Nowicki, Chelm (PL)

(73) Assignee: "HTL-STREFA" Spólka Akcyjna, Ozorków (PL)

( * ) Notice: Subject to any disclaimer, the term of this patent is extended or adjusted under 35 U.S.C. 154(b) by 469 days.

(21) Appl. No.: 12/063,635

(22) PCT Filed: Aug. 24, 2006

(86) PCT No.: PCT/PL2006/000057
§ 371 (c)(1), (2), (4) Date: Feb. 12, 2008

(87) PCT Pub. No.: WO2007/024152
PCT Pub. Date: Mar. 1, 2007

(65) Prior Publication Data
US 2008/0195134 A1    Aug. 14, 2008

(30) Foreign Application Priority Data
Aug. 25, 2005  (PL) ......................................... 376767

(51) Int. Cl.
*A61B 17/32* (2006.01)
*A61B 17/34* (2006.01)
(52) U.S. Cl. ........................................................ 606/181
(58) Field of Classification Search .................. 606/167, 606/181–183, 185; 604/110, 111, 117; 600/573, 600/583
See application file for complete search history.

(56) References Cited

U.S. PATENT DOCUMENTS

| | | | |
|---|---|---|---|
| 5,356,420 A | 10/1994 | Czernecki et al. | |
| 5,439,473 A | 8/1995 | Jorgensen | |
| 5,954,738 A * | 9/1999 | LeVaughn et al. | 606/181 |
| 6,390,990 B1 * | 5/2002 | Marshall et al. | 600/573 |
| 2003/0130597 A1 * | 7/2003 | Marshall | 600/583 |

FOREIGN PATENT DOCUMENTS

| | | |
|---|---|---|
| EP | 0 255 338 | 2/1988 |
| WO | WO 99/56622 | 11/1999 |
| WO | WO 2006/137752 A2 | 12/2006 |

OTHER PUBLICATIONS

International Search Report Dated Feb. 12, 2007.

* cited by examiner

*Primary Examiner* — Ryan Severson
*Assistant Examiner* — Katherine M Shi
(74) *Attorney, Agent, or Firm* — Plumsea Law Group, LLC

(57) ABSTRACT

A patient's skin puncturing device comprises a body (1), inside of which a puncturing needle (4) and at least one turned down arm (5, 6) are guided, and a push button (2). Between body (1) and button (2) activating elements (10, 11, 12, 13) are placed. Activating elements enable push button (2) to be forced into body (1) when a pre-set thrust force is exceeded. Needle (4) is driven by push button (2) by a membrane (9), which is broken after resting the needle (4) upon an abutting surface (16) in body (1). After breaking membrane (9) and the patient's skin puncture by the needle (4), needle (4) is withdrawn inwards the body (1) due to a transfer of a thrust force from push button (2) by turned down arm (5, 6) guided in the body (1).

14 Claims, 4 Drawing Sheets

PATIENT'S SKIN PUNCTURING DEVICE

TECHNICAL FIELD

The subject of the invention is a patient's skin puncturing device, particularly for collecting blood samples for diagnostic purposes.

BACKGROUND ART

From the U.S. Pat. No. 5,356,420 a puncturing device is known comprising a sleeve and a push button positioned at one sleeve end. The other sleeve end terminates with a bottom with an opening therein. Inside the sleeve a piston is slidably positioned, terminating with a push rod at the end closer to the push button, and with a puncturing tip at the end closer to the bottom opening. Inside the sleeve, between the push button face and the piston a drive spring is located, and between the piston and the sleeve bottom a return spring is placed. The piston comprises wings located on its outer perimeter, which wings rest on an internal projection of the sleeve, and when the device is used, the wings get broken, and subsequent re-use of the device is not possible.

In the U.S. Pat. No. 5,439,473 is disclosed a lancet designed for puncturing the patient's skin for collecting small blood samples. The lancet has an elongated body wherein a movable member is placed slidingly along the body axis, while the body has a top opening for the lancet push button, and a bottom opening for the piercing blade. The movable member consists of a flat spring, one end of which is joined to the push button. The push button has two upper arms perpendicular to its surface, and these arms have hooked ends placed in oblong openings of the body side walls. The other end of the movable member flat spring is joined with a holder wherein the piercing blade is fixed. The lower portion of the holder has two lower arms parallel to the upper arms. The lower arms have, moreover, upwardly directed, triangle shaped ends, which rest upon the lower edges of the oblong openings of the body walls. All parts of the movable member are made of plastic.

When the patient's skin is being punctured, the lancet push button is pressed, so the flat spring of the movable member is tensed, and hooked ends of the upper arms press against the ends of the lower arms of the movable member. Next, the lower arms get released, the flat spring rebounds, and the patient's skin is punctured by the piercing blade, which passes through the body bottom opening. After puncturing the skin, the flat spring assumes its free position, and the piercing blade retracts into the inside of the lancet body.

DISCLOSURE OF INVENTION

The purpose of this invention is to provide a patient's skin puncturing device, which is safe, both for the patient and for service personnel, simple and cheap, with a structure of a minimal number of components and devoid of driving and return springs and thus devoid of disadvantageous aspects connected with a presence of the springs in the puncturing devices.

The next purpose of this invention is to provide the patient's skin puncturing device with the structure, which guarantees getting a required minimal puncture energy and which enables the user, depending on needs, to regulate intuitively an energy of the puncture by a regulation of a speed of the pressure exerted by the user's finger on the push button.

The next purpose of this invention is to provide a patient's skin puncturing device of the structure forcing a reliable withdrawal of the needle from a wound without an increase in a number of device elements.

The essence of the patient's skin puncturing device according to the present invention built of a body, inside of which a puncturing needle and at least one turned down arm are guided, and a push button, whereas between the body and the push button activating elements are placed, and the activating elements enable to force the push button into the body when a pre-set thrust force is exceeded, is that the puncturing needle is driven by the push button by means of a membrane, which is broken after resting the puncturing needle upon an abutting surface in said body.

The essence of a variety of the patient's skin puncturing device, according to the invention, built of a body, inside of which a puncturing needle and at least one turned down arm are guided, and a push button, whereas between the body and the push button activating elements are placed, and the activating elements enable to force the push button into the body when a pre-set thrust force is exceeded, is that after breaking the membrane and the patient's skin puncture by the puncturing needle, the puncturing needle is withdrawn inwards the body due to a transfer of a thrust force from the push button by said turned down arm guided in the body.

Preferably, the patient's skin puncturing device, according to the invention, comprises a pair of turned down arms.

Preferably, the push button and the turned down arm constitute one component.

Preferably, the push button, the turned down arm and the sprayed round puncturing needle constitute one component.

Preferably, the push button has on its outer surface activating wings, which abut against internal protrusions in the body.

The advantage of the patient's skin puncturing device according to the invention is that it has the simplified two-components construction, which ensures the needle to be driven directly by the push button both during a puncture movement and during a needle withdrawal movement.

The lack of the driving and return springs eliminates all technical problems connected with their application in the known puncturing devices.

While usage of the patient's skin puncturing device according to the invention, the puncture takes place under the pressure of the user's finger, whereas the minimal puncture energy is guaranteed by a structurally determined value of a boundary pressure, which is connected with a value of a boundary force required to overcome a resistance protecting against the push button movement in the device body.

Simultaneously, depending on individual characteristics of the punctured skin, i.e. The skin thickness and hardness, the user can, by means of the regulation of the pressure speed, intuitively adjust the puncture energy transferred to the patient's body. Thus, the patient's skin puncturing device according to the invention guarantees to the user the certainty of the skin puncture, even in case of the very thick or hard skin.

The next advantage of the patient's skin puncturing device according to the invention is that it guarantees the certainty of the needle withdrawal when the skin is punctured and thereby ensuring a required operational safety of the device for the patient and for the medical personnel.

As a result, the solution of the patient's skin puncturing device according to the invention is safe while operation, structurally simple, cheap and easy in manufacture.

BRIEF DESCRIPTION OF DRAWINGS

The subject of the invention is presented in an example embodiment on the drawings, where.

BEST MODE OF CARRYING OUT THE INVENTION

Figure 1:
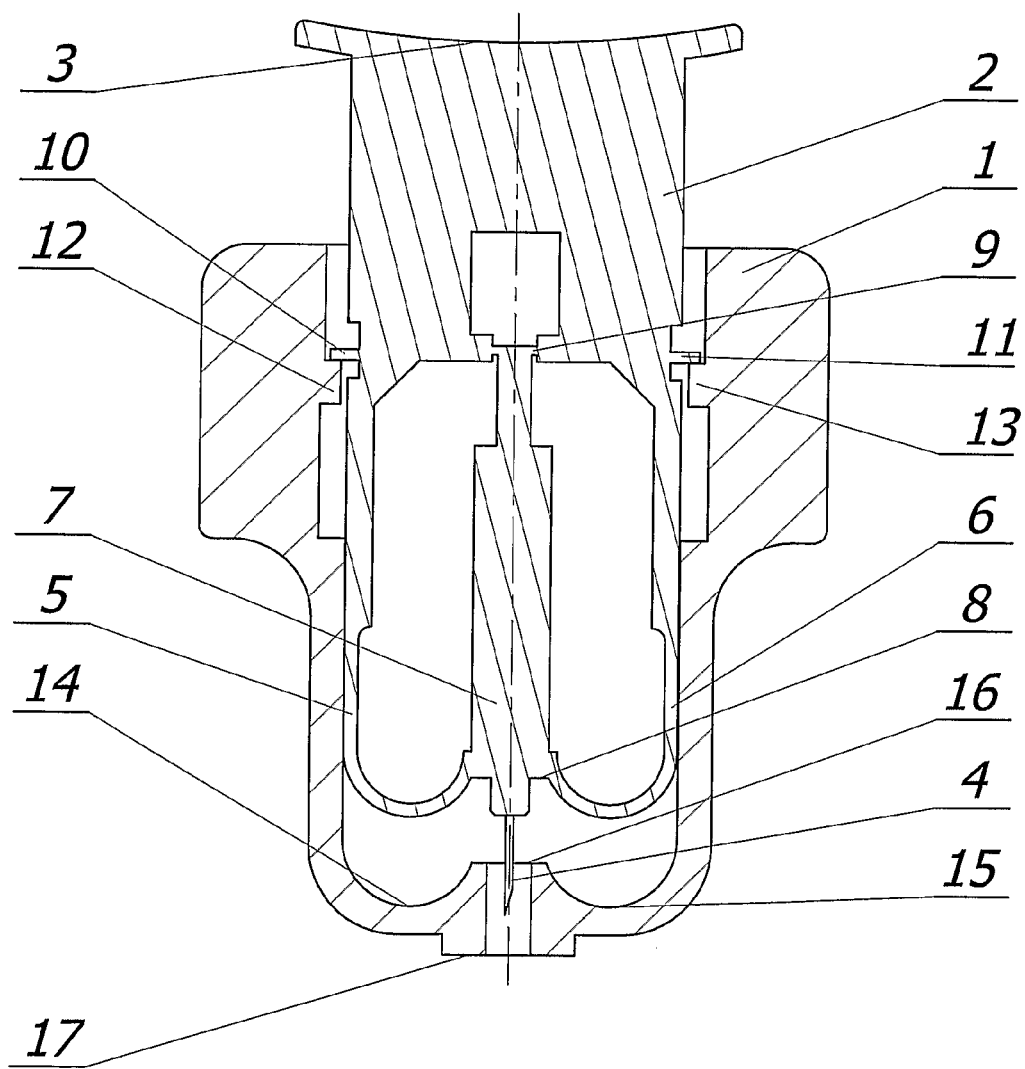
FIG. 1 shows the longitudinal view of the patient's skin puncturing device according to the invention, before its use, FIG. 2—the device of FIG. 1 after breaking off activating wings, FIG. 3—the device of FIG. 1 at a phase with a needle maximally protruding from a body of the device, and FIG. 4—the device of FIG. 1 after its use.

The patient's skin puncturing device according to the invention designed for collecting a sample of blood for diagnostic purposes, as shown in FIG. 1, is built of the body 1 and placed therein a push button 2. The push button 2 has a thrust face 3 in an upper portion and a puncturing needle 4 in a lower portion, whereas the upper and the lower portions of the push button 2 are, preferably, connected with each other by a pair of turned down and parallel to each other arms 5, 6 and by a support 7 placed in the axis of the push button 2. The support 7 has, respectively, a stop 8 of the puncturing needle 4 in the lower portion and a membrane 9 in the upper portion. Moreover, the push button 2 has on its outer surface two activating wings 10, 11, which abut against internal protrusions 12, 13 in the body 1. Further, underneath the turned down arms 5, 6 of the push button 2 the body 1 has inside two turned down surfaces 14, 15 and underneath the stop 8 of the puncturing needle 4 the body 1 has inside an abutting surface 16 of the stop 8 together with an opening for the puncturing needle 4 and from the side of the patient's skin abutting face 17.

FIG. 1 presents the device, according to the invention, in the standstill, it means before the activation, in which the two activating wings 10, 11 of the push button 2 rest on the internal protrusions 12, 13 of the body 1, the turned down arms 5, 6 are situated over the turned down surfaces 14, 15 of the body 1 and the puncturing needle 4 is situated in the body 1.

Figure 2:
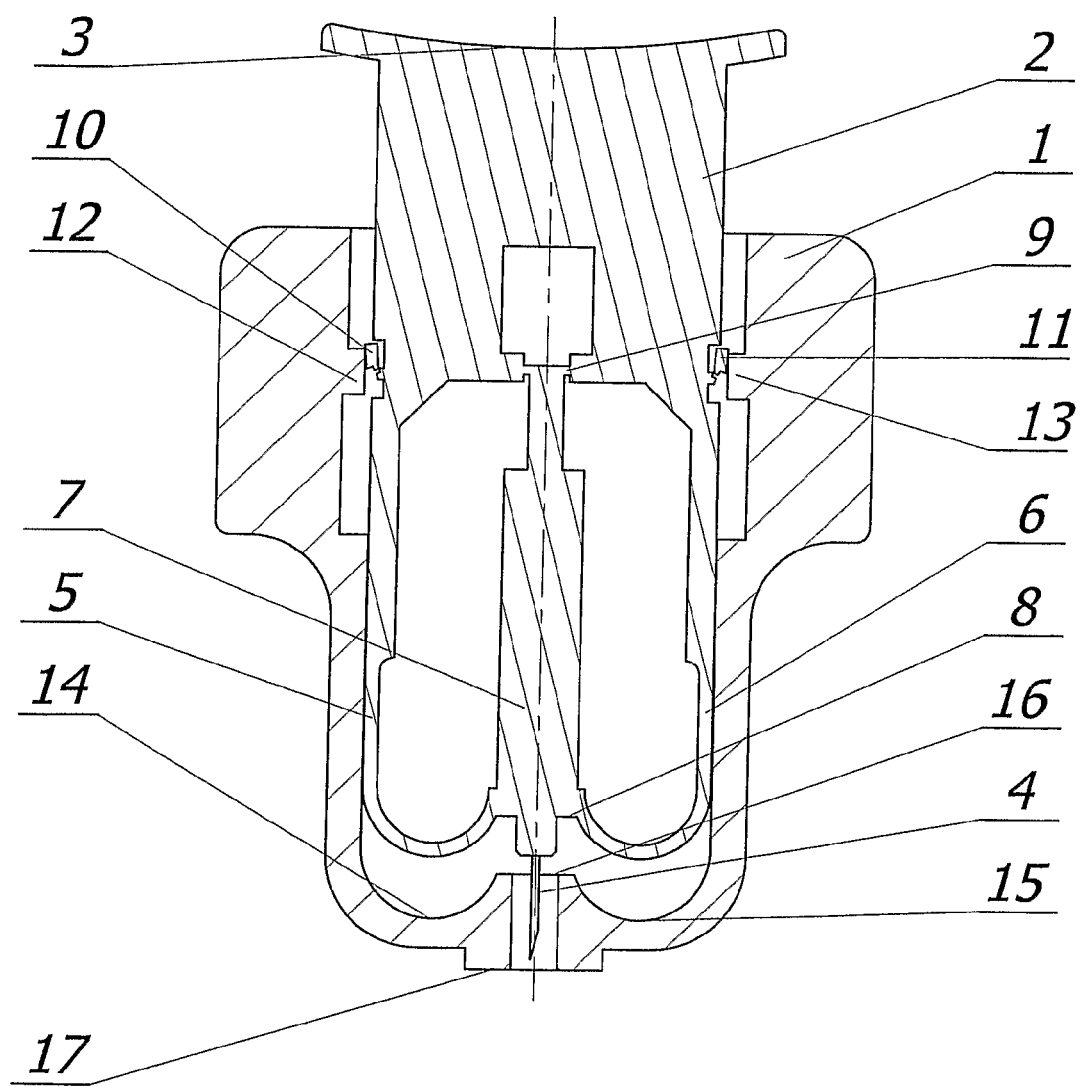

After applying to the thrust face 3 of the push button 2 a force, the value of which exceeds the boundary force determined by the construction of the device, the activating wings 10, 11 are broken off and, further, the push button 2 is moved downwards, the turned down arms 5, 6 bring closer to the turned down surfaces 14, 15 of the body 1 and the puncturing needle 4 moves progressively outside the body 1, as it is shown in FIG. 2.

Figure 3:
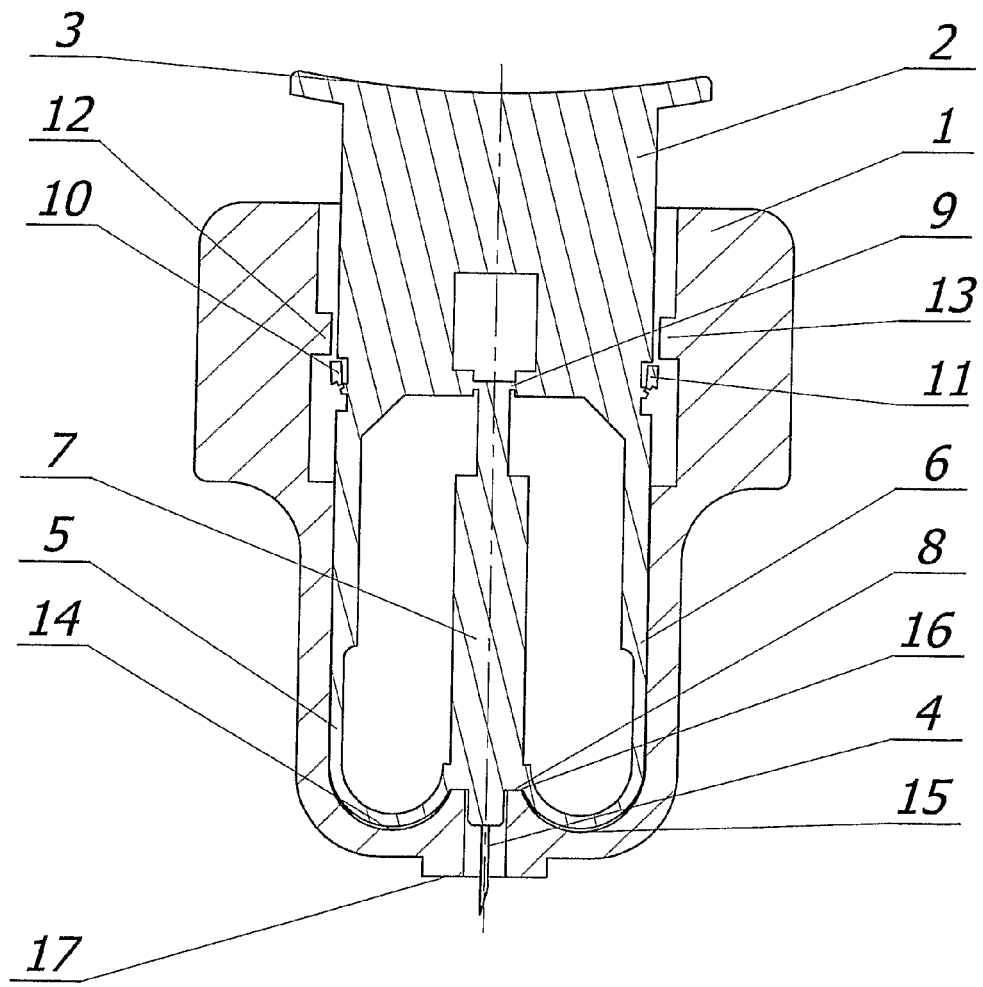

During further movement of the push button 2, as it is shown in FIG. 3, the puncture of the patient's skin by the puncturing needle 4 is performed and the stop 8 of the puncturing needle 4 abuts against the abutting surface 16. At the same time, the turned down arms 5, 6 strain and abut against the turned down surfaces 14, 15 of the body 1. The puncturing needle 4 is then situated in the lowest position, what causes the maximal puncture of the patient's skin.

Figure 4:
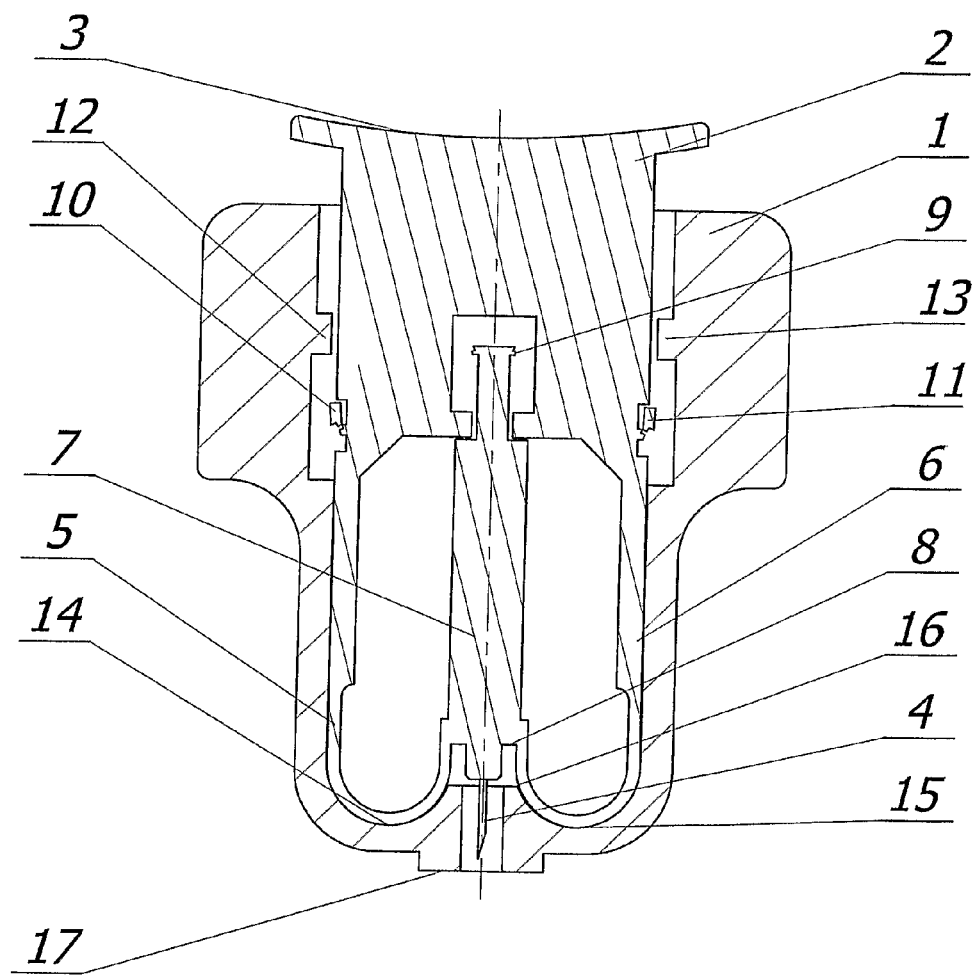

The next phase of the movement of the push button 2 is breaking the membrane 9 as result of turning down the arms 5, 6 upon the turned down surfaces 14, 15 of the body 1 and withdrawal the puncturing needle 4, as it is shown in FIG. 4. In consequence of this movement, the puncturing needle 4 retracts into the body 1 and does not protrude below the butting face 17 into the patient's skin thereby making the contact of the service personnel with the blood present on the needle impossible. The push button 2 is seized in the lower position by additional catches placed therein in order to make the moving of the puncturing needle 4 outside the body 1 as well as the contact with the blood collected impossible.

The device, according to the invention, is the disposable device insofar the broken off activating wings 10, 11 of the push button 2 make the subsequent use of the device impossible and the push button 2 is seized in the lower position.

We claim:

1. A patient's skin puncturing device comprising
a body, inside of which a puncturing needle and at least one deformable arm are guided, and
a push button,
whereas between said body and said push button activating elements are placed, said activating elements enable to force said push button into said body when a pre-set thrust force is exceeded, and the puncturing needle is driven by a thrust force in a puncturing direction applied by said push button by a membrane, which is broken after resting the puncturing needle on an abutting surface in said body,
wherein after breaking the membrane and the patient's skin puncture by the puncturing needle and during application of the thrust force, the puncturing needle is withdrawn inwards the body in a retracting direction opposite to the puncturing direction due to a transfer of the thrust force from the push button to the retracting direction by the at least one deformable arm being guided in the body and deformed to push the puncturing needle in the retracting direction,
wherein the push button and the at least one deformable arm are integrally formed with each other constituting one element.

2. A patient's skin puncturing device according to claim 1, wherein the at least one deformable arm comprises a pair of deformable arms.

3. A patient's skin puncturing device according to claim 1, wherein the push button, the at least one deformable arm, and a needle support member are integrally formed with each other constituting one element.

4. A patient's skin puncturing device according to claim 3, wherein the puncturing needle extends from the needle support member and wherein the needle support member is integrally formed between the at least one deformable arm and the membrane before the membrane is broken.

5. The patient's skin puncturing device according to claim 1, wherein the at least one deformable arm is guided in the body and deformed by the body such that the at least one deformable arm turns back on itself.

6. The patient's skin puncturing device according to claim 1, wherein the body comprises
a first end at which the push button is disposed, and
a second end that is opposite to the first end and from which the needle extends out of the body,
wherein after breaking the membrane, the at least one deformable arm slides against an interior wall of the second end of the body and moves in the retracting direction.

7. The patient's skin puncturing device according to claim 6, wherein the interior wall is curved when viewed in a cross-section of the body taken parallel to a longitudinal axis of the needle, and wherein the at least one deformable arm extends in the puncturing direction, turns against the curved interior wall, and extends in the retracting direction.

8. The patient's skin puncturing device according to claim 7, wherein the at least one deformable arm has a curved shape that matches the curved interior wall.

9. A patient's skin puncturing device comprising:
a body defining an interior compartment extending from a push button opening at a first end of the body to a needle opening at a second end of the body opposite to the first end, wherein the interior compartment is defined by an interior side wall of the body and an interior end wall at the second end of the body;

a push button disposed in the interior compartment and moveable within the interior compartment, wherein the push button has a first side closest to the interior end wall of the body and a second side opposite to the first side;

a deformable arm extending from the first side of the push button toward the interior end wall;

a needle support member disposed between the push button and the interior end wall and attached to the push button by a breakable member; and a needle extending from the needle support member and aligned with the needle opening, wherein movement of the push button in a puncturing direction from the first end of the body toward the second end of the body presses the needle support member against the interior end wall such that the breakable member breaks, allowing the needle support member to move in a retracting direction opposite to the puncturing direction in which the push button is moving, and wherein movement of the push button in the puncturing direction forces the deformable arm against the interior end wall such that the deformable arm turns back on itself and pushes the needle support member in the retracting direction.

10. The patient's skin puncturing device according to claim 9, wherein the push button and the deformable arm are integrally formed.

11. The patient's skin puncturing device according to claim 9, wherein the push button, the deformable arm, and the needle support member are integrally formed.

12. The patient's skin puncturing device according to claim 9, wherein the deformable arm turns back on itself and pushes the needle support member in the retracting position while the push button moves in the puncturing direction.

13. The patient's skin puncturing device according to claim 9, wherein the interior end wall is curved when viewed in a cross-section of the body taken parallel to a longitudinal axis of the needle, and wherein the deformable arm extends in the puncturing direction, turns against the curved interior wall, and extends in the retracting direction.

14. The patient's skin puncturing device according to claim 13, wherein the deformable arm has a curved shape that matches the curved interior wall.

* * * * *